United States Patent [19]

Melon et al.

[11] Patent Number: 5,308,579
[45] Date of Patent: May 3, 1994

[54] DEVICE FOR DISTRIBUTION OF THE LIQUIDS FOR AN APPARATUS FOR CLEANING, DISINFECTION AND LUBRICATION OF DENTISTRY HANDPIECES

[75] Inventors: Bernard Melon, Auxon Dessus, France; Bernhard Guggenheim, Erlenbach, Switzerland

[73] Assignee: Micro Mega SA, Besancon, France

[21] Appl. No.: 798,295

[22] Filed: Nov. 25, 1991

[30] Foreign Application Priority Data

Nov. 23, 1990 [FR] France ............... 90 14843

[51] Int. Cl.⁵ ................ B08B 3/02; B08B 3/04
[52] U.S. Cl. ........................... 422/28; 422/6; 422/29; 422/36; 422/116; 433/104; 433/116
[58] Field of Search ............ 422/28, 116, 6, 292, 422/295, 36, 29; 433/116, 104; 239/373, 423, 416.5, 566, 124

[56] References Cited

U.S. PATENT DOCUMENTS

| | | | |
|---|---|---|---|
| 4,070,424 | 1/1978 | Olson et al. | 239/124 |
| 4,116,382 | 9/1978 | Clerk | 239/373 |
| 4,752,444 | 6/1988 | Bowen et al. | 422/28 |
| 5,057,283 | 10/1991 | Guggenheim et al. | 422/116 |
| 5,065,942 | 11/1991 | Shannon | 239/429 |
| 5,122,344 | 6/1992 | Schmoegner | 422/28 |
| 5,137,689 | 8/1992 | Cantrell | 422/28 |

*Primary Examiner*—Robert J. Warden
*Assistant Examiner*—Ramon Torres
*Attorney, Agent, or Firm*—Weiser & Associates

[57] ABSTRACT

Liquids for cleaning, disinfecting and lubricating dentistry handpieces are distributed to the handpieces by a device which includes reservoirs for storing liquids for the cleaning, disinfection and lubrication procedures which are to take place, and a series of solenoid valves for sequentially opening at different stations according to a prescribed cycle. To this end, each liquid to be utilized is conveyed through each handpiece in actual liquid form, and not in an atomized form, and then atomized in the handpiece by compressed air entering through a conduit which is separate from the conduit for passing the liquids.

33 Claims, 3 Drawing Sheets

DEVICE FOR DISTRIBUTION OF THE LIQUIDS FOR AN APPARATUS FOR CLEANING, DISINFECTION AND LUBRICATION OF DENTISTRY HANDPIECES

BACKGROUND OF THE INVENTION

1. Field of the Invention

The present invention relates to a device for distribution of the liquids for an apparatus for cleaning, disinfection and lubrication of dentistry handpieces, the device being of the type in which the liquids are released, from their supply source or storage source, respectively, and are caused to penetrate and, if appropriate, pass through the handpieces arranged in the said apparatus, by means of solenoid valves opening sequentially at each station according to a chain cycle.

2. Description of Related Art

The dental surgeon must carry out systematically, at least daily, the cleaning, lubrication and sterilization or disinfection of the handpieces which he uses.

The different operations were hitherto carried out manually with the aid of various instruments, such as, for example, an aerosol spray, etc. These operations were tedious, and for this reason some practitioners did not carry them out with the necessary frequency, or did so imperfectly. It should also be noted that each handpiece had to be cleaned separately, which increased all the more the time spent.

In order to rectify this situation, autonomous apparatuses permitting the cleaning, disinfection and lubrication of dentistry headpieces have already been proposed. Such apparatuses are described, for example, in the patents or patent applications FR 2,618,357 and EP 0.300,945.

Experience shows that an acceptable cleaning and disinfection can be provided in a constant and satisfactory manner only if the periods of action of the corresponding fluids are perfectly constant and if the quantities of liquid passing through the handpieces are also constant themselves, regardless of the handpiece placed on one of the treatment stations. This constancy must be ensured from one station to another, from one treatment cycle to another, regardless of whether all the stations are in operation or whether one or more of them is (are) not in operation.

The embodiments described in the European Patent Application 0,300,945 does not make it possible to ensure this constancy with sufficient precision, despite the chain device which controls the outlet solenoid valves. Moreover, in this device, the reservoirs of liquid are under constant pressure as soon as the apparatus is in operation, which represents a danger if the operator has not properly closed the stopper of one of the reservoirs after the refilling operation.

SUMMARY OF THE INVENTION

It is therefore the principal object of the present invention to provide a device which remedies the above-mentioned disadvantages and is capable of ensuring a constant distribution of the treatment liquids.

The present invention relates to a device for distribution of the liquids for an apparatus for cleaning, disinfection and lubrication of dentistry handpieces, the device being of the type in which the liquids are released, from their supply source or storage source, respectively, and are caused to penetrate and pass through the handpieces arranged in the said apparatus, by means of solenoid valves opening sequentially at each station according to a chain cycle, characterized in that each liquid is conveyed under pressure as far as the handpiece in actual liquid form and not in spray form, and that the liquid is then atomised in the handpiece by compressed air entering via a conduit separate from the conduit for the entry of liquid.

An excellent precision is thus obtained as regards the quantity of liquid injected since, the pressure of the liquid being constant, the volume injected at each impulse depends only on the opening time of the passage, that is to say of the corresponding electrovalve; a time which can be controlled with great precision using microprocessor systems.

Another characteristic of the invention is that the air and liquid conduits can be connected via one and the same electrovalve of the type 3/2, allowing either the air or the liquid to pass, depending on the cycle in the chain.

A third essential characteristic of the invention is that the liquids are distributed in a star shape via conduits starting from a common point, this common point being connected to a solenoid valve device allowing either the water or the disinfectant to pass, and situated in reservoirs under pressure, and that the reservoirs under pressure are filled by gravity with the liquids contained in reservoirs not under pressure, the conduit from the reservoir not under pressure to the reservoir under pressure being provided with an anti-return device in such a way that the filling of the reservoir under pressure is carried out when the latter is not under pressure and stops automatically when the pressure is re-established therein.

BRIEF DESCRIPTION OF THE DRAWINGS

The invention will be better understood with the aid of the description which follows, of an embodiment given by way of a non-limiting example, with reference to the attached drawings, in which.

DETAILED DESCRIPTION OF THE INVENTION

Figure 1:
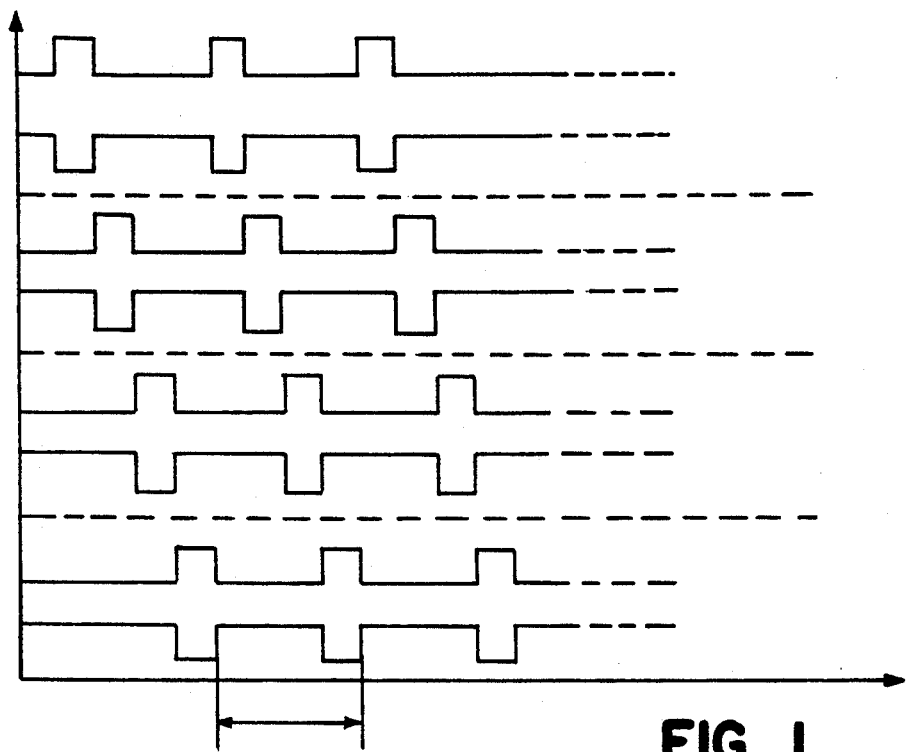
FIG. 1 is a representation of the chain functioning of the system for injection and atomising of the liquids for an apparatus with four stations.

FIG. 1 illustrates the principle of the chain functioning (cycling) for the injection and the atomising with (air) of the liquids for an apparatus with four stations. It shows the sequential aspect of a single cycle making it possible to treat each station successively before returning to the starting point of a new cycle.

Figure 2:
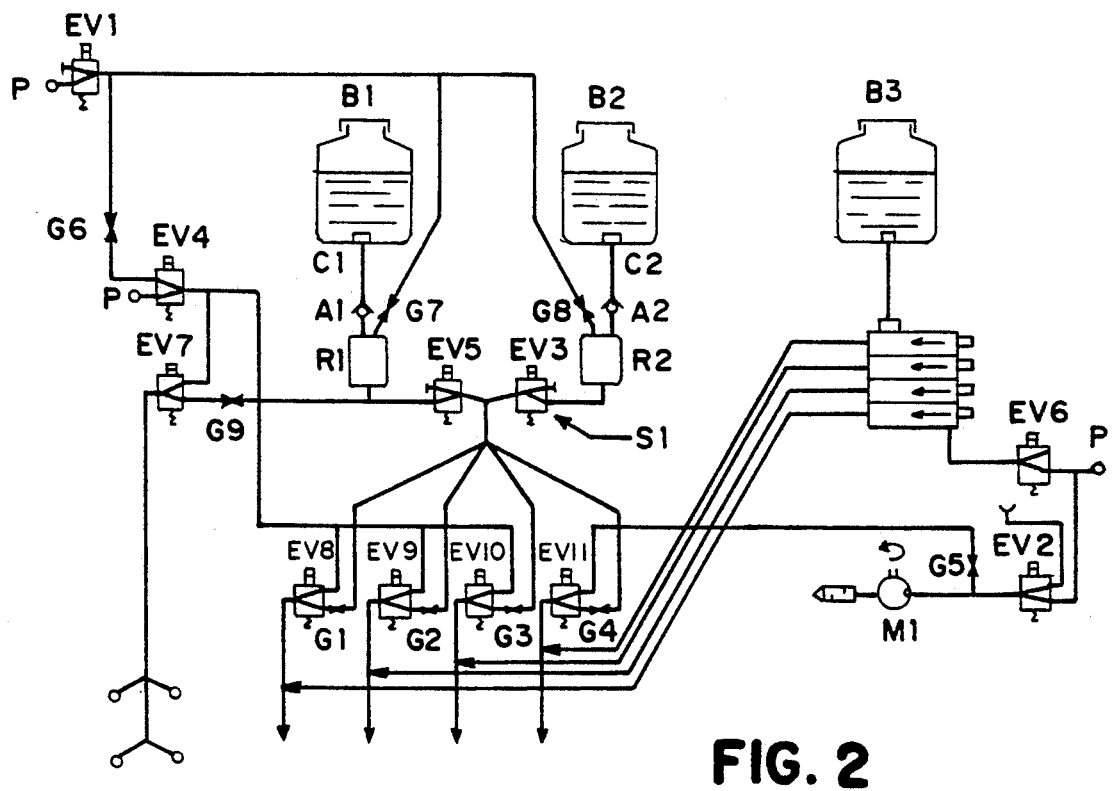
FIG. 2 represents the hydropneumatic scheme of one embodiment.

FIG. 2 shows the overall hydropneumatic scheme, which consists of two reservoirs B1 and B2 for disinfectant and water, respectively, at the bottom of which conduits C1, C2, each comprising an anti-return device A1 and A2, respectively, provide the connection with the reservoirs R1, R2. The reservoirs R1, R2 are capable of being placed under pressure by communicating, through a pair of jets G7 and G8, with the outlet of a valve EV1 connected to a compressed air system P.

The reservoirs R1 and R2 are connected to a selection device S1 permitting the passage either of the disinfectant or of the water; it being possible for S1 to be formed, as in the scheme shown in FIG. 2, by two flap solenoid valves EV3, EV5 of the type 2/5 or 3/2 (mounted as 2/2 or a piston electrovalve of the type the 3/2 mounted as 3/2). At the outlet of S1, a star-shape distribution permits the connection, via as many conduits as there are treatment stations (each provided with a jet G1, G2, G3, G4), to the solenoid valves EV8 to EV11 leading directly into the noses of the treatment stations; EV8 to EV11 are 3/2 solenoid valves, which could each be replaced by two 2/2 solenoid valves. The second inlet of the solenoid valves EV8 to EV11 corresponding to the treatment stations of mechanically drive handpieces is connected to the outlet of EV1.

In order to provide for two different flow rates of air, for example one for the atomising of the liquids or of the oil, and the other for the internal drying, it will be possible, as indicated in the diagram, to interpose a solenoid valve EV4, one of whose inlets is connected to the outlet of EV1 via a conduit provided with a jet G6, the other inlet being connected directly to the compress air system P.

In order to provide for the external treatment of the handpieces, a solenoid valve EV7 has one of its inlets connected through a jet G9 to the outlet of EV4 and the other either to the outlet of R1, if only disinfection is carried out externally, or to the outlet of R2, if only cleaning is carried out externally (shown in the illustrative FIG. 2), or else to the outlet of S1 if it is desired to carry out both, the outlet of EV7 supplying the external spray nozzles.

The electrovalve corresponding to the station receiving handpieces driven by air (e.g. turbines—there may be several of these) is connected by way of a conduit, comprising a jet G5, to the outlet of a solenoid valve EV2 also controlling the rotation of the air motor M1, which provides for the rotation of the handpieces. This makes it possible to provide for the rotation of the turbine at the same time as the motor M1 provides for the driving of the handpieces mounted on the other treatment stations, and at the same time to provide for the blowing such as that originating from EV4 for the other stations. The second inlet of EV2 is connected to a device (actuated by a solenoid valve EV6) for lubricating (dispersing oil from the reservoir B3) of the air motor, in such a way that this motor is lubricated only when it is not functioning. The device for lubricating of the handpieces is of the same type as that described in the patent application EP 0,300,945.

Figure 3A:
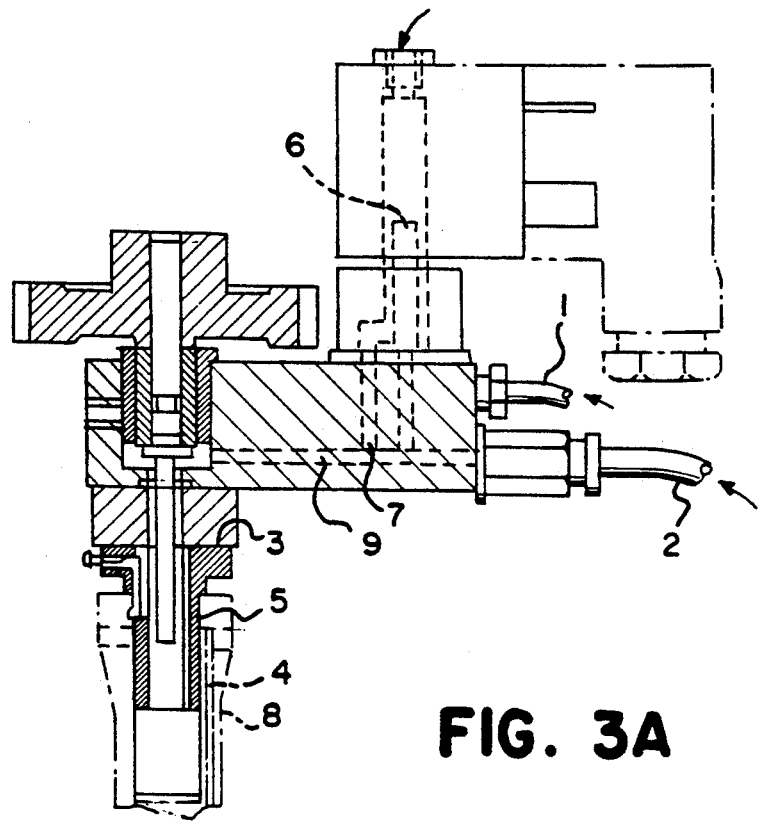
FIGS. 3A, 3B, 3C represent, in cross-section, the device of a treatment station of a handpiece other than an air turbine.
Figure 3B:
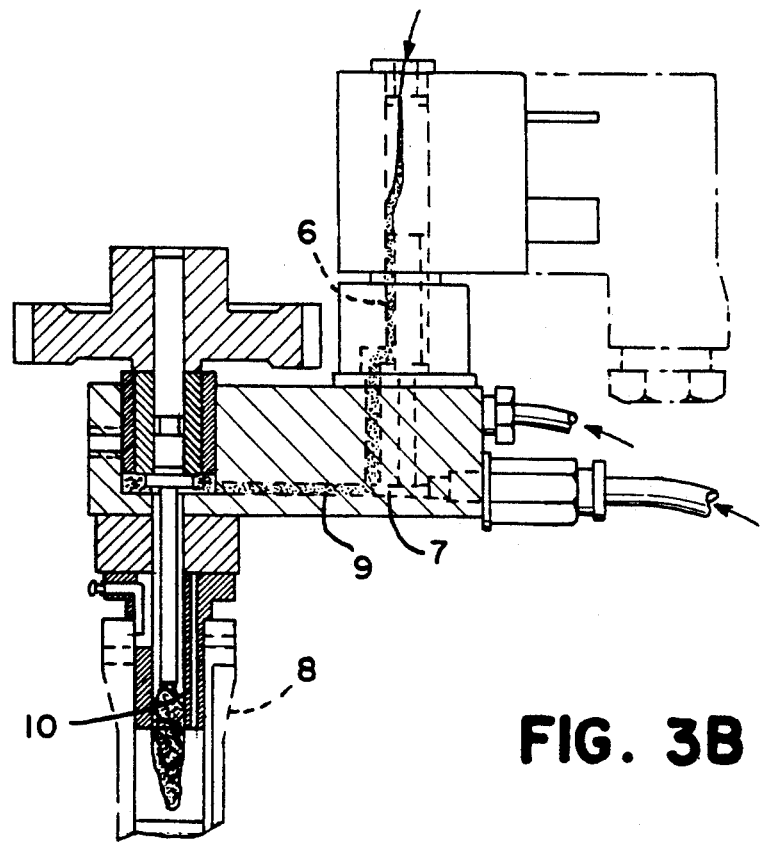
Figure 3C:
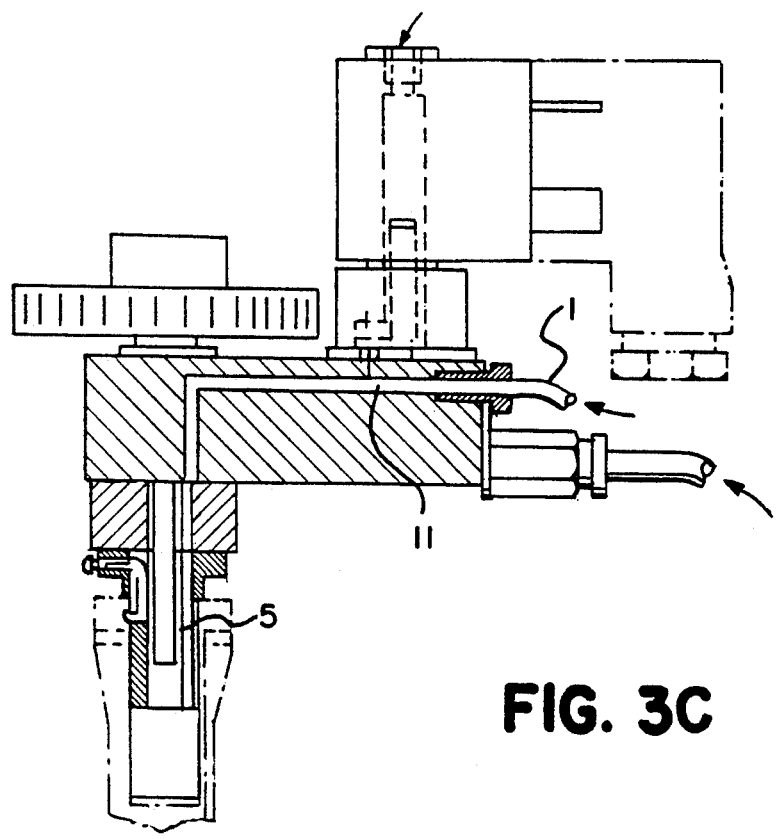

FIGS. 3A, 3B, 3C show a cross-section of the mechanical assembly at the level of the axis of a station for treatment of handpieces driven mechanically.

It will be noted that the oil follows, as far as the inlet of the handpiece, a path (1) completely independent of the path (2) for the water/disinfectant in such a way that, since the oil is injected only into a handpiece which has previously been dried with air, there is never an oil/disinfectant or oil/water mixture. Moreover, the support nose (3) is such that the oil can in no case penetrate into the spray channels (4) of the handpiece, since the path (1) leads onto the nose via a conduit (5) beyond the spray intakes (4).

FIG. 3A shows the position for injection of a quantity of water or alcohol (disinfectant), the air inlet being closed at (6).

In FIG. 3B, the intake of disinfectant is blocked at (7), and air is injected by opening at (6), the result of this being to displace the disinfectant towards and through the handpiece (8) via the conduits (9, 10), also with passage through the spray conduits (4).

FIG. 3C shows the path (1, 11, 5) of the oil, independent of that of the disinfectant.

Figure 4:
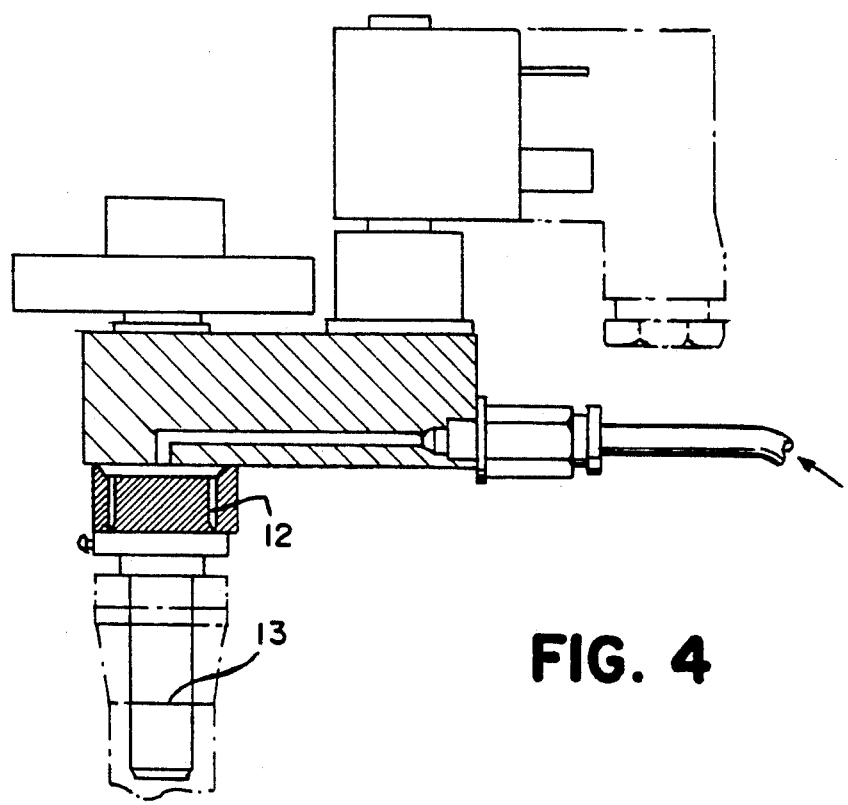
FIG. 4 represents, in cross-section, the spray device for external disinfection.

FIG. 4 shows the arrangement of the external spray nozzles. Four nozzles (12) are distributed about the axis (13) of the handpiece, in such a way that the conical jets provide for a wetting of all the external surfaces of the handpiece with alcohol by virtue of the electrovalve EV7.

On one of the rotating elements driven by the pneumatic motor, a rotation detector is provided, which can advantageously consist of a magnet fixed on a rotating part passing in front of a magnetic sensor. This device, governed by the microprocessor card which controls the whole of the apparatus, makes it possible at one and the same time to check for rotation of the motor and consequently of the handpieces, and also to check that the pressure does not drop below the functional threshold of the apparatus.

In order to prevent the apparatus from being started while the quantity of one of the liquids is no longer sufficient to ensure a complete treatment, the reservoirs R1 and R2 are defined in such a way that their contents permit one complete cycle to be carried out. Moreover, devices for detecting the presence of liquid are placed on the conduits for gravity descent, upstream of the anti-return flaps. It will be possible to use only one sensor, which will be placed judiciously on the conduit corresponding to the liquid with greater consumption. The sensor can be, for example, a capacitive sensor which permits the detection of the presence of liquid without another complementary element. When the presence of liquid is no longer detected, the apparatus will be able to finish the cycle in progress by virtue of the contents of R1 and R2 and will automatically be blocked at the command of the following cycle.

Several solenoid valves can be replaced by one or more solenoid valves ensuring overall the same functions, and this in order to limit the number of solenoid valves to be use.

We claim:

1. A device for distributing liquids in an apparatus for cleaning, disinfecting and lubricating dentistry handpieces, the device comprising:

a plurality of solenoid valve for sequentially opening at each of a plurality of stations according to a cycle wherein liquids are released from a source, for introduction into a conduit associated with each handpiece so that each liquid is conveyed under pressure and through each handpiece in actual liquid form and not in an atomized form; and a conduit associated with each handpiece for receiving compressed air and for delivering the compressed air to the handpiece, which is separate from the conduit for receiving the liquid, for atomizing the liquid only in the handpiece;

wherein the air conduit and the liquid conduit of each handpiece are connected by a single electrovalve associated with the handpiece, for selectively passing air and liquid depending upon the cycle of the distributing device.

2. The device of claim 1 wherein the electrovalve is a 3/2 type.

3. The device of claim 1 wherein the handpieces include a series of four external spray nozzles in communication with a conduit for introducing the liquids into each handpiece, and distributed about an axis of each handpiece.

4. The device of claim 3 wherein the external spray nozzles include means for developing conical jets for wetting all external surfaces of the handpiece.

5. The device of claim 1 wherein the handpieces include rotating elements driven by a pneumatic motor, and which further comprises a rotation detector arranged on each handpiece and including a magnet fixed on a rotating part of the handpiece, for passing in front of a magnetic sensor fixed on a stationary part of the handpiece.

6. The device for claim 5 wherein the rotation detector communicates with a microprocessor for controlling the apparatus for cleaning, disinfecting and lubricating, including means for checking for rotation of the handpieces, and means for checking that operating pressures do not drop below a functional threshold for the apparatus.

7. The device of claim 1 which further comprises means for lubricating the handpieces which includes a conduit for delivering oil to the handpieces along a path which is completely independent of the conduit for conveying the liquids, so that the oil does not mix with the liquids.

8. The device of claim 7 wherein the handpieces include a support nose having spray channels separate from portions of the support nose for delivering the oil.

9. The device of claim 8 wherein the portions of the support nose for delivering the oil extend beyond the spray channels of the support nose.

10. The device of claim 1 which further comprises a star-shaped distributor having an inlet formed at a common point and a plurality of outlets in communication with the electrovalves of the handpieces.

11. The device of claim 10 which further comprises a liquid selection valve in communication with the inlet of the star-shaped distributor.

12. The device of claim 11 which further comprises reservoirs which are capable of being pressurized, in communication with the liquid selection valve, for separately receiving water and disinfectant for delivery to the liquid selection valve.

13. The device of claim 12 which further comprises supply reservoirs which are not under pressure, in communication with the pressurizable reservoirs, for separately receiving the water and the disinfectant and for separately delivering the water and the disinfectant to the pressurizable reservoirs by gravity.

14. The device of claim 13 wherein the supply reservoirs communicate with the pressurizable reservoirs by a conduit which includes an anti-return device so that the pressurizable reservoirs are filled when not under pressure, and so that filling of the pressurizable reservoirs automatically stops when under pressure.

15. The device of claim 1 which further comprises two supply reservoirs, one for containing water and one for containing disinfectant; a conduit including an anti-return device extending from each of the supply reservoirs, and communicating with two reservoirs which are capable of being pressurized; means for pressurizing the reservoirs which are capable of being pressurized; selection means for delivering either the water or the disinfectant, in communication with the pressurizable reservoirs; and a star-shaped distributor for connecting the selection means with a first inlet of a plurality of control valves associated with the handpieces.

16. The device of claim 15 wherein the selection means includes two flap solenoid valves of the 2/2 type.

17. The device of claim 15 wherein the selection means includes two flap solenoid valves of the 3/2 type mounted as a 2/2 type.

18. The device of claim 15 wherein the selection means is a piston electrovalve of the 3/2 type mounted as a 3/2 type.

19. The device of claim 15 wherein the control valves are solenoid valves of the 2/2 type.

20. The device of claim 15 wherein the control valves are solenoid valves of the 3/2 type.

21. The device of claim 15 wherein at least some of the handpieces are air driven, and wherein the control valves of the air driven handpieces communicate, through a conduit including a jet, with means for controlling an air motor for rotating the air driven handpieces.

22. The device of claim 21 wherein the means for controlling the air motor for rotating the air driven handpieces includes an inlet communicating with means for lubricating the air motor so that the air motor is lubricated only when not functioning.

23. The device of claim 15 which further comprises means for preventing the apparatus for cleaning, disinfecting and lubricating from being operated when quantities of one of the liquids is no longer sufficient to ensure a complete treatment of the handpieces.

24. The device of claim 23 wherein the pressurizable reservoirs are sized to contain sufficient liquids for completing a full cycle of the distributing device.

25. The device of claim 24 which further comprises means for detecting the presence of liquids in the conduits connecting the supply reservoirs and the pressurizable reservoirs, upstream of the anti-return devices.

26. The device of claim 15 wherein at least some of the handpieces are mechanically driven, and wherein the control valves of the mechanically driven handpieces include a second inlet connected to the means for pressurizing the pressurizable reservoirs, for delivering pressurized air to the control valves of the mechanically driven handpieces.

27. The device of claim 26 wherein the means for delivering pressurized air to the control valves of the mechanically driven handpieces communicate with the water and the disinfectant only at the handpieces.

28. The device of claim 26 which further comprises means for delivering pressurized air having two different air flow rates, including a rate for atomizing a liquid and a rate for internal drying, to the control valves of the mechanically driven handpieces.

29. The device of claim 28 wherein the means for delivering pressurized air having two different air flow rates includes a solenoid valve having an outlet in communication with the control valves of the mechanically driven handpieces, and having a first inlet communicating through a jet with the means for pressurizing the pressurizable reservoirs and a second inlet communicating with a compressed air system.

30. The device of claim 28 which further comprises a solenoid valve for permitting external treatment of the handpieces, having a first inlet which communicates with the means for delivering pressurized air having two different air flow rates and a second inlet which communicates with the selection means for delivering either the water or the disinfectant, and having an outlet which communicates with a plurality of external spray nozzles associated with the

31. The device of claim 30 wherein the second inlet of the solenoid valve for permitting external treatment of the handpieces communicates only with an outlet of the pressurizable reservoir for receiving the water, when cleaning is to be performed externally.

32. The device of claim 30 wherein the second inlet of the solenoid valve for permitting external treatment of the handpieces communicates only with an outlet of the pressurizable reservoir for receiving the disinfectant, when disinfecting is to be performed externally.

33. The device of claim 30 wherein the second inlet of the solenoid valve for permitting external treatment of the handpieces communicates with outlets of both pressurizable reservoirs, when cleaning and disinfecting are to be performed externally.

* * * * *